United States Patent [19]

Glattstein

[11] Patent Number: 4,788,039

[45] Date of Patent: Nov. 29, 1988

[54] PROCESS AND TEST KIT FOR THE DETECTION OF EXPLOSIVES

[75] Inventor: Baruch Glattstein, Jerusalem, Israel

[73] Assignee: Erez Forensic Technology, Ltd., Israel

[21] Appl. No.: 108,280

[22] Filed: Oct. 14, 1987

[30] Foreign Application Priority Data

Oct. 15, 1986 [IL] Israel ..................... 80311

[51] Int. Cl.[4] ..................... G01N 31/22; G01N 33/00
[52] U.S. Cl. ..................... 422/61; 252/193; 436/110
[58] Field of Search ..................... 422/61, 56, 57, 86, 422/87, 88; 436/100, 103, 104, 106, 110, 111, 112, 113, 116, 164, 169, 815; 252/408.1, 193

[56] References Cited

U.S. PATENT DOCUMENTS 3,985,017 10/1976 Goldsmith ..................... 436/116
4,631,255 12/1986 Takino et al. ..................... 436/110

Primary Examiner—Barry S. Richman
Assistant Examiner—T. J. Wallen

[57] ABSTRACT

The invention provides a multi-reagent test kit for the presumptive identification of traces of explosives and/or discriminating between "innocent" material and explosive containing a first reagent comprising about 2.5 to 20% V/V of a tetra alkyl ammonium or phosphonium hydroxide in a solvent comprising at least 60% V/V dimethylsulfoxide and about 0 to 30% V/V methanol or water and a second reagent comprising a diazotization compound and a coupling compound of a Griess reagent pair.

7 Claims, No Drawings

PROCESS AND TEST KIT FOR THE DETECTION OF EXPLOSIVES

The present invention relates to a process and test kit for the presumptive field determination of traces of explosives, and discriminations between "innocent" material and explosive.

The increased use of explosives by terrorists is posing serious problems to law enforcement agencies, security personnel and airport authorities. Sending of exposive devices even as letter bombs, package bombs, luggage bombs through the mail and the use of explosive devices against both the civilian and military population has increased in certain nations.

It is known that small quantities of explosives are transferred to the hands during contact with commercial explosives or deposited on the outer surface of letter bombs and packages during the preparation of the explosive device. Most explosives used in the preparation of such a device have sufficient vapor pressure at ambient conditions to diffuse traces of these explosives to the surface. The detection of explosives in airport terminals, government buildings, embassies, aircraft and vehicles requires simple, portable and economical devices that can give a quick and positive identification of the presence of traces of explosives residue.

Some commerical chemical kits have been developed.

A. J. B. F. Lloyd, J. Forensic Science Society 7,198 (1976) described a chemical test kit in which a suspect material, on a microscope slide, is moistened with aqueous 0.1 1 sodium hydroxide and dried at 100° C. The slide is cooled and spotted with Griess' reagent, whereby a purple coloration is given by nitrate esters.

B. W. Fisco, American Journal of Forensic Sciencs 19, p. 141 (1974) describes a portable explosives identification kit for field use using a miniaturized TLC kit. This kit, however, requires a TLC plate, developing chamber, visualizer, chemical solvents, stoppered vials, labels, cottom swabs, spatulas, tweezers and probes.

C. F. T. Sweeney, P. W. O. Mitchell, U.S. Army Land Warfare Laboratory, Technical Report No. LWL-CR-24C74, June, 1974, describes the detection of a nitrate ester such as nitroglycerin and PETN by oxidizing action of nitric acid liberated by hydrolysis of the nitrate esters and color reaction with starch-KI by virtue of the liberation of iodine from the KI. Starch is sensitive indicator for iodine. The reaction is accomplished on filter paper under a heating lamp for two minutes.

All these described kits react very slowly and, require heat for the color formation, are time consuming and/or require technical training. This, of course, is a great disadvantage for field work.

The vast majority of military explosives contain one of the three following chemical groups:
(1) Polynitro aromatics such as 2,4,6-trinitrotoluene (TNT), Trinitrobenzene (TNB), picric acid and its derivatives;
(2) Nitrate esters such as Dynamite-nitroglycerin (NG) and ethyleneglycoldinitrate (EGDN) and Pentaerythrytol tetranitrate (PETN);
(3) Nitramines such as RDX, HMX and tetryl.

Contrary to the prior art approaches to the identification of explosives, it has now been surprisingly found that traces of explosives and/or discriminating between "innocent" material and explosive, can be detected when tetra-alkyl ammonium or phosphonium hydroxide is used as alkaline reagent in a solvent mixture of dimethylsulfoxide as a major solvent with or without water or methanol, instead of the alcoholic or aqueous alkaline solutions that were previously used, as a first explosive detection reagent. This change accelerates the -elimination reaction of nitrate esters, producing the preferred nitrite ions which can be readily detected by a second reagent that produces the well-known Griess reaction to produce a colored azo dye.

Nitramines, under the same conditions, undergo alkaline cleavage to form nitrite ions, which produce the same colored azo compound by the Griess reaction.

Polynitroaromatics form lightly colored (violet-dark) compounds upon reaction with this reagent (only with the first reagent).

Thus, the present invention provides a multi-reagent test kit for the presumptive identification of traces of explosives containing a first reagent comprising about 2.5 to 20% V/V of a tetra alkyl ammonium or phosphonium hydroxide in a solvent comprising of at least 60% V/V dimethylsulfoxide and about 0 to 30% V/V methanol or water and a second reagent comprising a diazotization compound and a coupling compound of a Griess reagent pair.

Preferably said first reagent comprises a tetra alkyl ammonium hydroxide in a solvent mixture of dimethylsulfoxide and methanol.

Especially preferred is a first reagent comprising about 75 to 90% V/V dimethylsulfoxide and 10 to 25% V/V of a 25 percent solution of a tetra alkyl ammonium hydroxide in methanol or water.

The second reagent contains modified Griess reagent comprised of two compounds in acidic medium. Griess reagent pairs that give high molar absorptivity are preferred, for example:
(1) p-aminobenzoic acid (compound A); N-phenyl-l-naphthylammine (compound B);
(2) p-Aminoacetophenone (compound A); N-phenyl-l-naphthylamine (compound B);
(3) Diaminodiphenylsulfone (compound A); N-phenyl-l-naphthylamine (compound B);
(4) p-Aminobenzonitril (compound A); N-phenyl-l-naphthylamine (compound B);
(5) Procaine (compound A); N,NM-Dimethyl-l-naphthylamine (compound B);
(6) Sulfanilamide (compound A); N-l-naphthylethylenediamine (compound B).

All the reagents are preferably prepared in 3–10% dilute acid. The concentration of the first compound is preferably between 2–8% and the concentration of the second compound is preferably between 0.1–2%.

These two reagents can be arranged in two tubes of chemical reagents. In light of the advantages and feasibility of an aerosol spray detector, these two reagents can be arranged in such a device.

The first reagent can be prepackaged in aerosol with Freon 12 as propellent. The second aqueous reagent can be prepackaged in aerosol with Freon 12 as propellent and Emcol 14 as emulsifier or with butane as propellent and Brij 92 as emulsifier.

The test kit can be used in various combinations:

I.
First Reagent: Tetra-alkylammonium hydroxide in DMSO-methanol mixture.
Second reagent: Compound A or B arranged together (short shelf life) or separately (long shelf life) in two separate vials in the same test tube, or in two aerosols.

II.
First reagent: As above.
Second reagent: Compound B incorporated in a dry sampling device such as filter paper, and A as above in vial or in spray.

III. Compound B incorporated in the first reagent.

The preferred compound A for diazotization is sulfanilamide. The preferred compound B for coupling is N-1-naphthyelthylene diamine. This couple gives the most satisfactory results. The preferred acid is phosphoric acid.

Examples of tetraalkyl ammonium or phosphonium hydroxides for use in the present invention include tetra-methyl, ethyl, pentyl, or butyl ammonium hydroxide and the analogue tetraalkyl phosphonium hydroxides.

The preferred tetra-alkylammonium hydroxide is tetrabutyl-ammoniumhydroxide.

The preferred concentration of compound A is 2.5% (W/V) and the preferred concentration of compound B is 0.2% (W/W)/

In case of using aerosol, preferred antifoam ingredients are 0.5% silicone antifoam and/or 5% isopropanol (V/V).

A preferred complete system involves three components, i.e., a dry sampling device such as filter paper and two chemical reagents.

The dry sampling device enables the technician to apply pressure against fingertips of suspects or other sampling surfaces. In special cases the aerosols can be applied directly on the surface without using a dry sampling device.

The first reagent reacts instantly with TNT and other polynitroaromatics. The second reagent, coupled with the first one, is very sensitive to the presence of nitrate-esters and nitramines. The appearance of certain colors indicates the presence of explosives. This test kit can detect microgram amounts of explosives.

While the invention will now be described in connection with certain preferred embodiments in the following examples so that aspects thereof may be more fully understood and appreciated, it is not intended to limit the invention to these particular embodiments. On the contrary, it is intended to cover all alternatives, modifications and equivalents as may be included within the scope of the invention as defined by the appended claims. Thus, the following examples which include preferred embodiments will serve to illustrate the practice of this invention, it being understood that the particulars shown are by way of example and for purposes of illustrative discussion of preferred embodiments of the present invention only and are presented in the cause of providing what is believed to be the most useful and readily understood description of formulation procedures as well as of the principles and conceptual aspects of the invention.

EXAMPLE 1

Composition of reagent No. 1: 85% DMSO, 11% methanol, 4% tetrabutylammonium hydroxide (V/V/V).

Composition of reagent No. 2: 8% sulfanilamide ad 0.5% N-(1-naphthyl)ethylenediamine dihydrochloride in 8% aqueous phosphoric acid.

A suspect material is put on filter paper. One drop of reagent No. 1 is added. If dark-violet color appears, it is an indication for TNT. If no color develops, one more drop of reagent 2 is added on the previous drop. If red-violet color appears, it is an indication for ester-nitrates such as PETN and dynamite and/or nitramine compounds such as RDX and HMX.

EXAMPLE 2

Composition of reagent No. 1: 80% DMSO, 15% methanol, 5% tetramethylammonium hydroxide (V/V/V)/

Composition of reagent No. 2: 5% p-aminobenzoic acid and 1% N-phenyl-1-naphthylamine in 5% aqueous hydrochloric.

The procedure of Example 1 is repeated with similar results.

EXAMPLE 3

Composition of reagent No. 1: 80% DMSO, 15% methanol, 5% tetrabutylphosphonium hydroxide (V/V/V).

Composition of reagent No. 2: 5% Procaine and 1% N-N-Dimethyl-1-naphthylamine in 50% aqueous acetic acid solution.

The procedure of Example 1 is repeated with similar results.

EXAMPLE 4

Reagent 1:
A prepackaged aerosol spray:
35 ml of stock solution composed of:
25 ml DMSO;
6 ml of $CH_3OH$;
4 ml Tetrabutylammonum hydroxide
0.1 gr N-1-naphthylethylene diamine.

Reagent 2: 35 ml of 2.5% sulfanilamide in 5% aqueous phosphoric acid in packed with 15 gr Freon 12 using 0.5 gr Emcol-14 as emusifier.

A suspect material is put on filter paper. The filter paper is sprayed by reagent 1. If dark-violet color appears, it is an indication for TNT. If no color develops, the same filter paper is sprayed over by reagent 2. If red-violet color appears, it is an indication for ester nitrates such as PETN and dynamite and/or nitramine compounds such as ROX and HMX.

EXAMPLE 5

A prepackaged aerosol spray:
Reagent 1:
35 ml of stock solution composed of:
30 ml of DMSO;
2.5 ml of $CH_3OH$
2.5 ml of Tetrabutylammonium hydroxide. All the ingredients are packed with 15 gr Freon. is packed with 15 gr Freon.

Reagent 2:
35 ml of 2.5% sulfanilamide in 5% aqueous phosphoric acid is packed with 10 gr butane using 0.5 gr Brij-92 as emulsifier.

Filter paper is bathed with 1.0% N-1-naphthylethylene diamine dihydrochloride in water solution and air dried for a few minutes.

The procedure of example 4 is repeated.

It will be evident to those skilled in the art that the invention is not limited to the details of the foregoing illustrative examples and that the present invention may be embodied in other specific forms without departing from the essential attributes thereof, and it is therefore desired that the present embodiments and examples be considered in all respects as illustrative and not restrictive, reference being made to the appended claims, rather than to the foregoing description, and all changes which come within the meaning and range of equivalency of the claims are therefore intended to be embraced therein.

What is claimed is:

1. A multi-reagent test kit for the presumptive identification of traces of explosives, said kit containing a first reagent comprising about 2.5 to 20% V/V of a tetra alkyl ammonium or phosphonium hydroxide in a solvent comprising at least 60% V/V dimethylsulfoxide and about 0 to 30% V/V of methanol or of water; and a second reagent comprising a diazotization and a coupling Griess reagent pair.

2. A multi-reagent test kit for the presumptive identification of traces of explosives according to claim 1 wherein said first reagent comprises a tetra alkyl ammonium hydroxide in a solvent mixture of dimethylsulfoxide and methanol.

3. A multi-reagent test kit for the presumptive identification of traces of explosives according to claim 1 comprising about 75 to 90% V/V dimethylsulfoxide and 10 to 25% V/V of a 25 percent solution of a tetra alkyl ammonium hydroxide in methanol or water.

4. A multi-reagent test kit for the presumptive identification of traces of explosives according to claim 1 wherein said first reagent comprises tetra butyl ammonium hydroxide.

5. A multi-reagent test kit for the presumptive identification of traces of explosives according to claim 1 wherein said second reagent comprises sulfanilamide and N-1-naphthylethylenediamine.

6. A multi-reagent test kit for the presumptive identification of traces of explosives according to claim 1 wherein both components of said second reagent are each incorporated in a dilute acid.

7. A multi-regent test kit for the presumptive identification of traces of explosives according to claim 6 wherein said acid is phosphoric acid.

* * * * *